United States Patent [19]

Giudicelli et al.

[11] 4,031,094
[45] June 21, 1977

[54] N-META-TRIFLUOROMETHYLPIPERA-ZINES

[75] Inventors: Don Pierre René Lucien Giudicelli, Fontenay-sous-Bois; Henry Najer, Paris, both of France

[73] Assignee: Synthelabo, Paris Cedex, France

[22] Filed: Jan. 22, 1976

[21] Appl. No.: 651,274

Related U.S. Application Data

[60] Division of Ser. No. 402,783, Oct. 2, 1973, Pat. No. 3,954,763, which is a continuation-in-part of Ser. No. 349,869, April 10, 1973, abandoned.

[30] Foreign Application Priority Data

Apr. 10, 1972 France .............................. 72.12442

[52] U.S. Cl. ......................... 260/268 PH; 424/250
[51] Int. Cl.² ....................................... C07D 295/14
[58] Field of Search ............... 260/268 PH, 268 CN

[56] References Cited

UNITED STATES PATENTS 3,954,763  5/1976  Giudicelli et al. ........... 260/268 PH Primary Examiner—Donald G. Daus
Assistant Examiner—Jose Tovar
Attorney, Agent, or Firm—Stevens, Davis, Miller & Mosher

[57] ABSTRACT

Compounds particularly useful in view of their anorexigenic and anxiolytic properties are provided which are the N'-alcoxycarbonylalkyl, N'-cyanoalkyl and N'-carboxyalkyl derivatives of N-meta-trifluoromethylphenylpiperazine.

2 Claims, No Drawings

N-META-TRIFLUOROMETHYLPIPERAZINES

CROSS REFERENCE TO RELATED APPLICATIONS

This application is a division of Ser. No. 402,783, filed on Oct. 2, 1973, now U.S. Pat. No. 3,954,763, issued May 4, 1976, which is a continuation-in-part of abandoned Ser. No. 349,869, filed on Apr. 10, 1973.

INVENTION OF THE PARENT APPLICATION

This section describes the invention of the parent application; U.S. Ser. No. 402,783 (herein the parent invention) which is directed to the starting compounds for the invention of present application:

The parent invention provides N-(m-trifluoromethylthio-phenyl)-piperazine having the formula

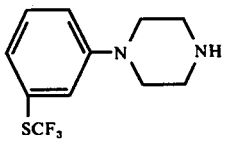

(I)

and its salts with inorganic acids (e.g. hydrochloric acid) or organic acids.

The compound of formula I can be prepared by reacting m-trifluoromethylthio-aniline with diethanolamine, in the presence of a halohydric acid such as hydrochloric acid.

The reaction is carried out at high temperature, preferably at 180° to 240° C, for several hours, preferably 3 hours.

The inorganic and organic salts of the N-(m-trifluoromethylthio-phenyl)-piperazine are prepared by the generally known methods.

Finally, the parent invention comprises the industrial applications of the compound (I) and its salts and more particularly their use as intermediates for synthesis.

The examples which follow illustrate the invention.

EXAMPLE 1

N-(m-trifluoromethylthio-phenyl)-piperazine

In a 500 ml three-neck flash equipped with a thermometer, a gas bubbling tube and a reflux condenser, are introduced 38.6 g (0.2 mol) of m-trifluoromethylthio-aniline and 21 g (0.2 mol) of freshly distilled diethanolamine.

A hydrochloric acid flow is bubbled in the mixture for about 40 minutes. The reaction mixture is heated for 1 hour at 180° C. A hydrochloric acid flow is again introduced for 30 minutes, the temperature being maintained at 200° C. The reaction is completed by heating for 1 hour and a half at 240° C. The mixture is allowed to cool and then poured into 100 ml of water. The red solution is alkalized by a 40% caustic soda lye, extracted three times with 100 ml of chloroform each time. The chloroform extracts are washed with 100 ml of water, dried on calcium chloride and filtered off, and then the solvent is evaporated from the filtrate. The oily residue is rectified. The fraction which passes over between 80° and 130° C/4 mm is collected and again rectified.

17.4 g (yield = 33%) of N-(m-trifluoromethylthiophenyl)-piperazine are finally obtained, in the form of a colourless liquid passing over at 118°–121° C/3 mm, which is soluble in water and in most usual organic solvents. $n_D^{25} = 1.545$

|  |  | Analysis $C_{11}H_{13}F_3N_2S$ (252); |  |  |  |  |
|---|---|---|---|---|---|---|
| Calculated | % C | 50,37 | H | 4,96 | N | 10,68 |
| Found | % | 49,78 |  | 4,82 |  | 10.47 |

EXAMPLE 2

N-(m-trifluoromethylthio-phenyl)-piperazine hydrochloride

The N-(m-trifluoromethylthio-phenyl)-piperazine is dissolved in anhydrous ether. A dry hydrochloric acid flow is bubbled in the solution. The precipitated hydrochloride is filtered off and recrystallised in isopropylic alcohol. It is in the form of a white crystalline compound which is soluble in water. Melting point: 134° C.

|  |  | Analysis $C_{11}H_{14}F_3Cl\ N_2S$ (298.5) |  |  |  |  |  |  |
|---|---|---|---|---|---|---|---|---|
| Calculated | % C | 44,23 | H | 4,72 | N | 9,38 | F | 19,08 | Cl | 11,87 |
| Found | % | 44,23 |  | 4,89 |  | 9,42 |  | 19,10 |  | 11,87 |

The compound (I), having an aromatic nucleus, may be used as a coupler for the preparation of disazo dyestuffs. For example, it may be substituted for N-phenyl-thiomorpholine-S-dioxide in the process of Example IB of Wallace & al, U.S. Pat. No. 3,379,711, to yield a water insoluble compound capable of being fixed to polyethylene terephtalate via the usual dispersion techniques.

SUMMARY OF THE INVENTION

The present invention provides, as new compounds, the piperazine derivatives of the formula:

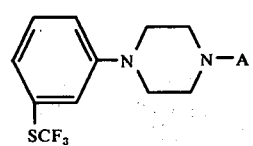

(IA)

in which A represents either a group —(CH$_2$)$_n$—COOR where n is an integer from 1 to 6 and R is a straight or branched alkyl radical of 1 to 6 carbon atoms, or a group —CH$_2$—(CH$_2$)$_n$—R$_1$ where n is as hereinbefore defined and R$_1$ is CN or COOH, and the pharmaceutically acceptable salts thereof, particularly their acid addition salts with pharmaceutically acceptable mineral and organic acids, and, where R$_1$ is COOH, their salts with non-toxic mineral and organic bases, e.g. the sodium and amine salts.

DETAILED DESCRIPTION OF THE INVENTION

According to a feature of the invention, the compounds of formula (IA) made by reacting N-(m-trifluoromethylthiophenyl)-piperazine with a halogeno compound of the formula A-X in which X is chlorine, bromine or iodine and A is as hereinbefore defined. The reaction may be carried out by heating the two starting materials together in an inert organic solvent such as benzene or chloroform in the presence of an acceptor for the hydrohalic acid liberated, for example an alkali metal carbonate or hydride or an organic base such as triethylamine or diethylaniline.

A still further method for making the compounds of formula I in which A is $CH_2—(CH_2)_n—CN$ comprises reacting a compound of the formula:

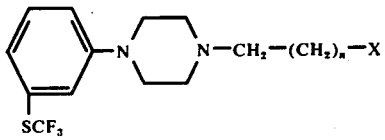

(IV)

in which X is as hereinbefore defined, with a metallic cyanide such as cuprous, potassium or sodium cyanide. The compounds of formula IV may be prepared by the reaction of a halogenation agent, for example thionyl chloride, thionyl bromide, phosphorus trichloride, or phosphorous tribromide, with an alcohol of the formula:

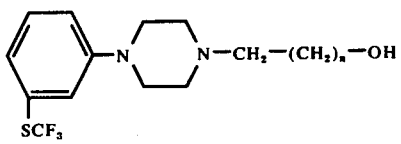

(V)

itself obtained by reacting N-(m-trifluoromethylthiophenyl)-piperazine with a halogeno alcohol of the formula $X—CH_2—(CH_2)_n—OH$ in which $n$ and X are as hereinbefore defined.

The salts of the compounds of formula IA may be prepared by known methods for the preparation of salts of bases and carboxylic acids.

The compounds of formula IA and their salts have interesting pharmacological properties which make them of therapeutic interest. They have in particular anorexigenic and anxiolytic properties, for example, N-(β-cyanoethyl)-N'-(m-trifluoromethylthiophenyl)-piperazine hydrochloride (hereinafter referred to as compound IA' has been compared experimentally with N-(m-trifluoromethylphenyl)-piperazine (compound II), known to possess anorexigenic and anxiolytic properties, and N-(m-trifluoromethylthiophenyl)-piperazine (compound III) known to possess anorexigenic properties. The tests used were:

1. a study of the anorexigenic effects in the rat trained to satisfy its alimentary needs in a period of 5 hours each 24 hours;
2. the motor activity in mice in the hour following administration of the compound under test;
3. the electric "battle test" (Tedeschi & al, J. Pharmacol., 1959, 125, pages 28–24); and
4. potentiation or sleep caused by hexabarbital in an intraperitoneal dose of 175 mg/kg.

In every case, the compounds under test were administered orally. The results obtained are given in the table below which also gives the LD 50's (and their 95% confidence limits) of the compounds studied determined intravenously and orally.

| Compound | II | III | IA' |
|---|---|---|---|
| Anorexia ED 50 (mg/kg) | 25 | 15 | 11 |
| Motor Activity (5 mg/kg) | − 45 % | 0 | 0 |
| Electric Battle Test ED 50 (mg/kg) | 15 | 15 | 8 |
| Potentiation of sleep caused by hexobarbital | ++++ | ++++ | ++++ |
| LD 50 (mg/kg) intravenously | 80 (74–86) | 90 (80–100) | 180 (169–191) |
| orally | 200 (180–220) | 210 (184–239) | 335 (307–366) |

These results show that compound IA', the compound of the present invention, possesses a better therapeutic index than compounds II and III since it has, overall, a higher activity and a lower toxicity.

The compounds of formula IA and their non-toxic salts, and especially the aforesaid compound IA' and its non-toxic salts, can therefore be used an anorexigenics and anxiolytics, for example in the treatment of obese patients who, as is well known, often suffer from anxiety. The invention therefore includes within its scope a pharmaceutical composition comprising one or more compounds of formula IA or non-toxic salts thereof in association with a compatible pharmaceutically acceptable carrier, especially a carrier such as to fit the composition for oral administration. These compositions may also contain other pharmacologically active compounds besides the compounds of formula IA which are therapeutically and pharmaceutically compatible with the latter. Suitable compositions for oral administration are solid compositions such as tablets, pills, capsules and powders. Each dosage unit ordinarily contains from 1 to 50 mg of active agent and the daily oral dosage of the latter is usually between 1 and 150 mg of an adult.

EXAMPLE 3

N-(β-cyano-ethyl) N'-(m-trifluoromethylthiophenyl)-piperazine.

N-(m-trifluoromethylthiophenyl)-piperazine (10.8 g, 0.047 g.mol.) and acrylonitrile (4.9 g, 0.094 g. mol.) are introduced into a 50 ml round bottomed flask provided with a stirrer and a reflux condenser. 0.1 ml of a 40% solution of benzyltrimethylammonium hydroxide in methyl alcohol is added with cooling and stirring. The mixture is allowed to stand at ambient temperature for 2 days and then heated for 2 hours to 80° C. After cooling, anhydrous diethyl ether (100 ml) is added to the reaction mixture, insoluble materials are filtered off, and the solution obtained evaporated on a water-bath in vacuo. The residue is fractionally distilled and N-(β-cyano-ethyl)-N'-(m-trifluoromethylthiophenyl)-piperazine (11 g, 88% yield) is thus obtained as a clear yellow viscous liquid, b.p. 198°–200°/3 mm Hg, $n_D^{23}$ = 1.5378.

| | Analysis $C_{14}H_{18}F_3N_3S$ (M.W.315) : | | | |
|---|---|---|---|---|
| Calculated | % : C | 53.32 | H | 5.11 |
| Found | % : | 53.23 | | 5.02. |

EXAMPLE 4

N-(β-cyano-ethyl)-N'-(m-trifluoromethylthiophenyl)-piperazine hydrochloride.

N-(β-cyano-ethyl)-N'-(m-trifluoromethylthiophenyl)-piperazine (10.2 g) is dissolved in anhydrous diethyl ether (100 ml) and hydrogen chloride gas is passed into the solution until precipitation of the salt formed ceases. The hydrochloride is separated and recrystallised from isopropyl alcohol. N-(β-cyano-ethyl)-N'-(m-trifluoromethylthiophenyl)-piperazine hydrochloride (6.7 g) is thus obtained as a white crystalline solid, m.p. 140° C, which is soluble in water.

| | Analysis $C_{14}H_{17}ClF_3N_3S$ (M.W. 352) | | | | | |
|---|---|---|---|---|---|---|
| Calculated | % : C | 47.80 | H | 8,87 | F | 16.20 | Cl | 10.08 |
| Found | % : | 48.04 | | 8.68 | | 16.09 | | 10.13 |

EXAMPLE 5

N-(β-methoxycarbonyl-ethyl) N'-(m-trifluoromethylthiophenyl)-piperazine hydrochloride.

N-(m-trifluoromethylthiophenyl)-piperazine (7 g, 0.0267 g.mol) and freshly distilled methyl acrylate (2.55 g, 0.0295 g.mol.) are introduced in a 50 ml round bottomed flask provided with a stirrer and reflux condenser. The temperature rises slightly. The mixture is allowed to cool and 0.1 ml of a 40% solution of benzyl-trimethylammonium hydroxide in methyl alcohol is then added with stirring. The mixture is allowed to stand for 2 days at ambient temperature. Boiling isopropyl alcohol (60 ml) is then added and the mixture is acidified by addition of concentrated hydrochloric acid (2.3 ml). The solvents are removed on a water-bath in vacuo and the residue is treated twice with benzene (50 ml each time) which is distilled off to remove water azeotropically. The residue is then taken up in isopropyl alcohol (50 ml) and the solution is filtered hot and allowed to stand several hours in a refrigerator. The precipitate formed is separated and dried in vacuo over phosphorous pentoxide. N-(β-methoxycarbonyl-ethyl)-N'-(m-trifluoromethylthiophenyl)-piperazine hydrochloride (8.2 g, 80% yield) is thus obtained as a white crystalline powder, m.p. 180° C, soluble in water.

| | Analysis $C_{15}H_{20}F_3ClN_2O_2S$ (M.W. 385): | | | | | | | | | | |
|---|---|---|---|---|---|---|---|---|---|---|---|
| Calculated | % : C | 46.82 | H | 5.24 | F | 14.81 | Cl | 9.21 | N | 7.28 |
| Found | % : | 46.88 | | 5.28 | | 14.63 | | 9.17 | | 7.30. |

What we claim is:
1. A compound of the formula:

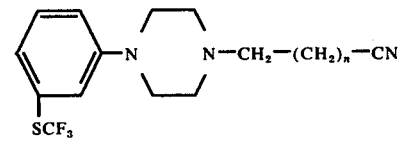

wherein n is an integer from 1 to 6 and the pharmaceutically acceptable salts thereof.
2. A compound of claim 1, wherein n is 1.

* * * * *